US005981706A

United States Patent [19]

Wallen et al.

[11] Patent Number: 5,981,706

[45] Date of Patent: Nov. 9, 1999

[54] METHODS FOR SYNTHESIZING HEAT SHOCK PROTEIN COMPLEXES

[75] Inventors: Erik S. Wallen; Pope L. Moseley, both of Albuquerque, N.Mex.

[73] Assignee: University of New Mexico, Albuquerque, N.Mex.

[21] Appl. No.: 08/986,234

[22] Filed: Dec. 5, 1997

Related U.S. Application Data

[63] Continuation-in-part of application No. 08/717,239, Sep. 20, 1996, Pat. No. 5,747,332, and application No. 08/934,139, Sep. 19, 1997.

[51] Int. Cl.[6] .............................. C07K 3/00; C07K 17/00

[52] U.S. Cl. .......................... 530/350; 530/412; 530/413; 530/402; 435/803; 210/656

[58] Field of Search .................................... 530/412, 413, 530/402, 350; 435/803; 210/656

[56] References Cited

U.S. PATENT DOCUMENTS

| | | | |
|---|---|---|---|
| 5,114,852 | 5/1992 | Yabusaki et al. | 435/189 |
| 5,132,407 | 7/1992 | Stuehr et al. | 530/395 |
| 5,268,465 | 12/1993 | Bredt et al. | 435/252.3 |
| 5,320,941 | 6/1994 | Young et al. | 435/7.23 |
| 5,348,864 | 9/1994 | Barbacid | 435/69.1 |
| 5,541,095 | 7/1996 | Hirschberg et al. | 435/172.3 |
| 5,550,214 | 8/1996 | Eberlein et al. | 530/328 |
| 5,614,192 | 3/1997 | Vandenark | 424/185.1 |
| 5,830,464 | 11/1998 | Srivastava | 424/93.71 |
| 5,837,251 | 11/1998 | Srivastava | 424/193.1 |

OTHER PUBLICATIONS

Baltz, "Vaccines in the treatment of Cancer," *Am. J. Health–Syst. Pharm.* (1995), 52:2574–2585.

Beckmann et al., "Interaction of Hsp70 with newly synthesized proteins: implactions for protein folding and assembly," *Science* (1990), 248:850–4.

Blachere et al., "Heat Shock Protein Vaccines Against Cancer," *Journal of Immunotherapy,* (1993), 14:352–356.

Buchner, "Supervising the Fold: Functional Principals of Molecular Chaperones," the FASEB Journal, vol. 10, pp. 10–19, Jan. 1996.

Gao et al., "Effect Constitutive 70–kDa Heat Shock Protein Polymerization on Its Interaction with Protein Substrate" in *The Journal of Biological Chemistry,* vol. 271 (1996), 28: 16792–16797.

Georgopoulos et al., "Role of the Major Heat Shock Proteins as Molecular Chaperones," Annu. Rev. Cell Biol. 1993, pp. 602–634.

Gjertsen et al., "Vaccination with mutant ras peptides and induction of T–cell responsiveness in pancreatic carcinoma patients carrying the corresponding RAS mutation," *Lancet* (1995), 346:1399–1400.

Heike et al., "Heat shock protein–peptide complexes for use in vaccines," *Journal of Leukocyte Biology* (1996), 60:153–8.

Lefkovits, *Immunological Methods Manual,* vol. 2, Chapter 9.11, (San Diego: Academic Press, 1997).

Lehninger, *Biochemistry,* (New York: Worth Publishers, 1970), p. 299.

Li et al., "Tumor rejection antigen gp96/grp94 is an ATPase: implications for protein folding and antigen presentation," *The EMBO Journal,* vol. 12, No. 8 (1993), 143–3151.

Li et al., "A Critical Contemplation on the Roles of Heat Shock Proteins in Transfer of Antigenic Peptides During Antigen Presentation," *Behring Inst. Mitt.* (1994), 94:37–47.

Moseley, "Mechanisms of heat adaptation: Thermotolerance and acclimization" in *J. Lab. Clin. Med.* (1994), 123:48–52.

Nandan et al., "A rapid single–step purification method for immunogenic members of the hsp family: validation and application," *Journal of Immunological Methods* (1994), 176:255–263.

Old, "Immunotherapy for cancer, " *Scientific American* (1996), 275–142.

Palleros et al., "Interaction of hsp70 with unfolded proteins: Effects of temperatures and nucleotides on the kinetics of binding" in *Proc. Natl. Acad. Sci.* (Jul. 1991), 88:5719–5723.

Palleros et al., "hsp70–Protein Complexes" in *The Journal of Biological Chemistry,* vol. 269 (1994), 18:13107–13114.

Roman et al., "Synthetic peptides non–covalently bound to bacterial hsp70 elicit peptide specific T–cell responses in vivo," *Immunology,* (1996), 88:487–492.

Roman et al., "Delayed–type hypersensitivity elicited by synthetic peptides complexed with *mycobacterial tuberculosis* hsp70," *Immunology,* (1997), 90:52–56).

Srivastava, "Peptide–Binding Heat Shock Proteins in the Endoplasmic Reticulum: Role in Immune Response to Cancer and in Antigen Presentation," *Advances in Cancer Research* (1993), 62:153–177.

Srivastava et al., "Heat shock protein–peptide complexes in cancer immunotherapy," *Current Opinion in Immunology* (1994), 6:728–732.

Srivastava et al., "Heat shock proteins transfer peptides during antigen processing and CTL priming," *Immunogenetics* (1994), 39:93–98.

Srivastava, "Heat shock proteins in immune responses to cancer: the fourth paradigm," *Experientia* (1994), 50:1054–1060.

Udono et al., "Heat Shock Protein 70–associated Peptides Elicit Specific Cancer Immunity," *J. Exp. Med.* (1993), 178–1391–1396.

Udono et al., "Comparison of Tumor–Specific Immunogenicities of Stress–Induced Proteins gp96, hsp90, and hsp 70," *Journal of Immunology* (1994), 5398–5403.

Welch et al., "Rapid Purification of Mammalian 70,000–Dalton Stress Proteins: Affinity of the Proteins for Nucleotides," *Molecular and Cellular Biology* (Jun. 1985), 1229–1237.

*Primary Examiner*—Cecilia J. Tsang
*Assistant Examiner*—C. Delacroix-Muirheid
*Attorney, Agent, or Firm*—Jagtianai & Associate

[57] ABSTRACT

The present invention provides a method for synthesizing heat shock protein-peptide complexes comprising the steps of: adding a shock protein to a denatured protein matrix to bind the heat shock protein to the denatured protein matrix; and adding a complexing solution comprising a peptide to elute a heat shock protein-peptide complex. The present invention also provides a heat shock protein-peptide complex synthesized by the method of the invention. In addition the present invention provides an apparatus for synthesizing heat shock protein-peptide complexes comprising a heat shock protein complex bound to a denatured protein matrix.

23 Claims, 5 Drawing Sheets

Table 1

| Protein | Amino Acid Sequence |
|---|---|
| Prostate Specific Antigen | Amino acids 146-154, 41-150 and 154-163 |
| VP1 protein of foot and mouth disease | Amino acids 135-159 |
| Leishmaniasis protein GP63 | Amino acids 467-482 |
| MAGE-1 | EADPTGHSY |
| Feline Immunodeficiency Virus Protein V3 | RAISSWKQRNRWEWRPD |
| | RAISSWKQRN |
| | SWKQRNRWEW |
| | QRNRWEWRPD |
| Foot and mouth disease proteins | IMDRFVKINSLSPTHVIDL |
| | PFGHLTKLELPTDHH |
| | SIINNYYMQQYQNSM |
| Mutant P53 tumor suppressor protein | TYSPALKNMFYQLAKTCPVQLKMFYQLAKTCPVQL |
| | KMFYQLAKTCPVQL |
| | FYQLATCPV |
| | FLQLAKTCPV |
| Human papillomavirus | Amino acids 49-57 |
| Human immunodeficiency virus protein gp160 | RIQRGPGRAFVTIGK |
| | RIHIGPGRAFYTTKN |
| | SITKGPGRVIYATGQ |
| | TLHMGPKRAFYATGN |
| | SIHIGPGRAFYTTGE |
| Human immumodeficiency virus peptide | RIHIGPGRAFYTTKN |
| Human immunodeficiency virus V3 peptides | SIRIGPGKVFTAKGG |
| | SISIGPGRAFFATTD |
| | RIHIGPGRAFYTTKN |
| | SLSIGPGRAFRTREI |

Fig. 1A

Table 1 (continued)

| | |
|---|---|
| | GIAIGPGRTLYAREK |
| | SITKGPGRVIYATGQ |
| | RVTLGPGRVWYTTGE |
| | SIHIGPGRAFYATGD |
| | SIYIGPGRAFHTTGR |
| | RIQRGPGRAFVTIGK |
| | GIHFGPGQALYTTGI |
| | STPIGLGQALYTTRG |
| | STPIGLGQALYTTRI |
| | RTPTGLGQSLYTTRS |
| Hepatitis C proteins | |
| NS5 | MSYSWTGACVTPCAAF |
| viral core protein | GFADLMGYIPLVGAPL |
| | LMGYIPLVGA |
| mutated RAS | KLVVVGAXGVGKSALTI |
| peptide from chlamydia trachomatis | TINKPKGYTGKE |
| Human Immunodeficiency proteins | |
| Gag | HIVWASRFL |
| | ILGQLQPSL |
| | SLQTGSEEL |
| | ELRSLYNTV |
| | SLYNTVATL |
| | EIKDTKEAL |
| | TLNAWVKVV |
| | DLNTMLNTV |

Fig. 1B

Table 1 (continued)

| | |
|---|---|
| | DIAGTTSTL |
| | TLQEQIGWM |
| | EIYKRWILL |
| | IILGLNKIV |
| | FMMTACGV |
| | VLAEAMSQV |
| | PIDKELYPL |
| Pol | LLTQIGCTL |
| | PIETVPVKL |
| | ALVEICTEM |
| | GIRYQYNVL |
| | YIYQYMDDL |
| | KIEELRQHL |
| | ELHPDKWTV |
| | DIQKLVGKL |
| | KLKRGTKAL |
| | ELAENREIL |
| | ILKEPVHGV |
| | PLVKLWYL |
| | ELQAIYLAL |
| | YLALQDSGL |
| | ALQDSGLEV |
| | LIKKEKVYL |
| | HLEGKVILV |
| | ELKKIIGQV |
| | PLWKGPAKL |

Fig. 1C

Table 1 (continued)

| | |
|---|---|
| | LLWKGEGAV |
| | IIRDYGKQM |
| | |
| Vif | MIVWQVDRM |
| | RIRTWKSLV |
| | DLADQLIHL |
| | KIKPPLPSV |
| | |
| Env gp120 | MICSATEKL |
| | IILSWDQSL |
| | KLTSLCVSL |
| | KLTSCNTSV |
| | VITQACPKV |
| | IIVQLNTSV |
| | TLKQIASKL |
| | AIINMWQKV |
| | |
| Env gp41 | FLGAAGSTM |
| | TLTVQARQL |
| | GIVQQQNNL |
| | AIEAQQHLL |
| | QLQARILAV |
| | RILAVERYL |
| | GIWGCSGKL |
| | QIWNHTTWM |
| | YIKLFIMIV |
| | FIMIVGGLV |

Fig. 1D

Table 1 (continued)

| | |
|---|---|
| | MIVGGLVGL |
| | GLRIVFAVL |
| | SIRLVNGSL |
| | RLVNGSLAL |
| | SLALIWDDL |
| | LIWDDLRSL |
| | RLRDLLLIV |
| | LLLIVTRIV |
| | LIVTRIVEL |
| | LLQYWSQEL |
| | ELKNSAVSL |
| | LLNATAIAV |
| Vpr | AIIRILQQL |
| | IIRILQQLL |
| Rev | YLGRSAEPV |
| | QILVESPTV |
| | ILVESPTVL |
| Vpu | QIAIVAALV |
| Nef | GMDDPEKEV |

Fig. 1E

METHODS FOR SYNTHESIZING HEAT SHOCK PROTEIN COMPLEXES

RELATED APPLICATIONS

The present application is a continuation-in-part of U.S. patent application Ser. Nos. 08/717,239 Pat. No. 5,747,332, filed Sep. 20, 1996 and application No. 08/934,139, filed Sep. 19, 1997 the entire disclosure and contents of which are hereby incorporated by reference.

This invention is made with government support under contract number: DAMD-17-95-C-5093, awarded by the United States Department of the Army. The government may have certain rights in this invention.

BACKGROUND OF THE INVENTION

1. Field of the Invention

The present invention relates generally to methods for synthesizing heat shock protein-peptide complexes.

2. Description of the Prior Art

Heat shock proteins (HSPs) are associated in cells with a broad spectrum of peptides, polypeptides, denatured proteins and antigens with which they form complexes. These complexes form as part of the cell's normal protein manufacturing process as described in Beckmann et al., "Interaction of Hsp70 with newly synthesized proteins: implications for protein folding and assembly" in *Science* (1990), 248: 850–4. HSP-peptide complexes may also be formed as part of the transport of peptides to the MHC class I molecules on the cell's surface as described in Srivastava et al., "Heat shock proteins transfer peptides during antigen processing" in *Immunogenetics* (1994), 39: 93–98. When purified from autologous tumors, such HSP-peptide complexes have been useful in vaccines against cancers and infectious diseases as described in Srivastava et al., "Heat shock protein-peptide complexes in cancer immunotherapy" in *Current Opinion in Immunology* (1994), 6: 728–732; and Srivastava, "Peptide-Binding Heat Shock Proteins in the Endoplasmic Reticulum" in *Advances in Cancer Research* (1993), 62: 153–177. Vaccination with antigenic peptides alone can elicit an immune response but peptides bound to HSPs appear to elicit a much more efficient response. In this regard, Srivastava has estimated in Srivastava, "Heat shock proteins in immune responses to cancer: the fourth paradigm" in *Experientia* (1994), 50: 1054–1060, and that 10 $\mu$g of gp96 isolated from tumor cells may be complexed with approximately 10 pg of peptide representing a tumor-associated mutation. While 10 pg of peptide cannot be used to successfully vaccinate an animal against a subsequent tumor challenge, 10 pg of peptide complexed with gp96 is enough to elicit protection.

Several types of cancer vaccines that are currently being investigated, including heat shock protein vaccines, have been described in Old, "Immunotherapy for cancer" in *Scientific American* (1996), 275: 142. These potential vaccines have included: inactivated cancer cells and their extracts which can jump-start the immune system (particularly cancer cells engineered to secrete cytokines, such as IL-2 or GM-CSF, similarly heighten anti-tumor immunity and cells designed to express co-stimulatory molecules, such as B-1, enhanced the ability of T-cells to recognize tumor cells); tumor peptides, fragments of tumor proteins recognized by T-cells, which can be injected alone or with immune-boosting adjuvants; injected tumor proteins which are taken up by antigen-presenting cells and break them down into a range of peptide fragments recognized by T-cells; dendritic cells, antigen-presenting cells which are isolated from the blood, exposed to tumor peptides or engineered to produce tumor proteins and then reinjected; gangliosides, which humans can produce antibodies against and which are found on the surface of tumor cells; viral and bacterial vectors, genes coding for tumor antigens which are incorporated into viral or bacterial genomes, that, when injected, draw immunity against themselves and encoded antigens; and DNA and RNA coding for tumor antigens which prompt normal cells to begin producing these antigens.

The heat shock protein vaccines consist of HSP-peptide complexes purified from tumor cells containing a mixture of peptides as described by Udono and Srivastava in "Heat shock protein 70-associated peptides elicit specific cancer immunity" in *Journal of Experimental Medicine* (1993), 178: 1391–6. Most of the peptides complexed with HSPs and isolated from tumor cells are presumably portions of normal cellular proteins. Therefore, the HSP-peptide complexes need to be purified at fairly high levels in order to obtain HSPs complexed with peptide portions of mutated oncogenes. Because many of the purified peptides are portions of normal cellular proteins, vaccination with these purified complexes may incur the risk of auto-immune disorders.

Peptide vaccination experiments use peptide sequences of known tumor mutations such as described in Gjertsen et al., "Vaccination with mutant ras peptides and induction of T-cell responsiveness in pancreatic carcinoma patients carrying the corresponding RAS mutation" in *Lancet* (1995), 346: 1399–1400. Peptide vaccination experiments are also being tried with viral diseases such as described in Kelleher et al., "Safety and immunogenicity of UB1 HIV-IMN octameric V3 peptide vaccine administered by subcutaneous injection" in *AIDS Research & Human Retroviruses* (1997), 13: 29–32 are currently receiving much attention.

HSP-peptide complexes have been purified from autologous tumors and used for vaccination against the same tumor. It has been anticipated that material purified in this way can also be used for vaccination against human tumors in Srivastava and Udono, "Heat shock protein-peptide complexes in cancer immunotherapy" in *Current Opinion in Immunology* (1994), 6: 728–32. The use of these purified complexes in treating patient tumors would require the isolation of tumor material from each individual patient. This is not practical or even possible for many types of tumors. Many types of cancer, however, have well-defined mutations in specific genes. The use of de novo HSP-peptide complexes allows the use of HPS-peptide vaccines without the need for removing a portion of the tumor. The de novo complexes also allow prophylactic vaccination against a variety of diseases using peptides representing known oncogenic mutations or peptides representing portions of known viral proteins.

Bacterial hsp70-peptide complexes, created by incubating purified HSPs together with a synthetic peptide solution have also been used to stimulate peptide specific T-cell responses (See Roman et al., "Synthetic peptides non-covalently bound to bacterial hsp70 elicit peptide specific T-cell responses in vivo," *Immunology*, (1996), 88: 487–492, and Roman et al., "Delayed-type hypersensitivity elicited by synthetic peptides complexed with mycobacterial tuberculosis hsp70 ," *Immunology*, (1997), 90: 52–56).

In general, previous heat shock protein purifications have had two goals. The first goal has been to obtain pure HSPs without any contaminating peptides or proteins as described in Welch et al., "Rapid purification of mammalian 70,000-dalton stress proteins: affinity of the proteins for nucleotides" in *Molecular and Cellular Biology* (1985), 5: 1229–1237 and in Nandan et al., "A rapid single-step purification method for immunogenic members of the hsp family: validation and application" in *Journal of Immunological Methods* (1994), 176: 255–263. The second goal has been to purify the intracellular HSP-peptide complexes as described in Udono et al., "Heat shock protein 70-associated peptides elicit specific cancer immunity" in *Journal of Experimental Medicine* (1993), 178: 1391–1396.

However, the fact that previously described methods only produce HSPs already complexed with intracellular peptides or stripped of their associated peptides is a serious deficiency. Also, there is no known simple way of synthesizing purified HSP-peptide complexes.

SUMMARY OF THE INVENTION

The present invention provides a method of creating HSP-peptide combinations that will increase the effectiveness of peptide-based vaccines and allow more flexibility of use than the current HSP-based vaccines which require isolation of material from a portion of the tumor itself. Although several authors have described systems in which HSP vaccines might be used, including: Blachere et al., "Heat shock protein vaccines against cancer" in *Journal of Immunology* (1993), 14: 352–56; Heike et al., "Heat shock protein-peptide complexes for use in vaccines" in *Journal of Leukocyte Biology* (1996), 60: 153–8; and Srivastava, "Heat shock proteins in immune response to cancer: the fourth paradigm" in *Experientia* (1994), 50: 1054–60; Roman et al., "Synthetic peptides non-covalently bound to bacterial hsp70 elicit peptide specific T-cell responses in vivo," *Immunology*, (1996), 88: 487–492; Roman et al., "Delayed-type hypersensitivity elicited by synthetic peptides complexed with mycobacterial tuberculosis hsp70, *Immunology*, (1997), 90: 52–56; none of these authors have speculated on the usefulness of purifying the proteins and synthesizing the complexes in a single step.

In one embodiment, the present invention provides a method for synthesizing heat shock protein complexes comprising the steps of: adding a heat shock protein to a denatured protein matrix to bind the heat shock protein to the denatured protein matrix; and adding a complexing solution comprising a peptide to elute a heat shock protein-peptide complex.

The present invention further provides a heat shock protein-peptide complex made according to the method of the invention. Preferably, the heat shock protein-peptide complex is an ADP-heat shock protein-peptide complex.

The present invention further provides an apparatus for synthesizing ADP-heat shock protein-peptide complexes comprising an ADP-heat shock protein complex bound to a denatured protein matrix.

Other objects and features of the present invention will be apparent from the following detailed description of the preferred embodiments.

BRIEF DESCRIPTION OF THE DRAWINGS

The invention will be described in conjunction with the accompanying drawings, in which:

FIGS. 1A to 1E are a table showing peptides suitable for use in a preferred embodiment of the invention.

DETAILED DESCRIPTION OF THE PREFERRED EMBODIMENTS

Definitions

For the purposes of the present invention the term "peptide" refers to all types of peptides and conjugated peptides including: peptides, proteins, polypeptides, protein sequences, amino acid sequences, denatured proteins, antigens, oncogenes and portions of oncogenes.

For the purposes of the present invention the term "individual" refers to an individual person or animal from whom a cell lysate, heat shock protein, or peptide is obtained.

Description

In a preferred embodiment the invention provides a method for synthesizing HSP-peptide complexes. In this method, HSP complexes are bound to a denatured protein matrix or column. Then a complexing agent, such as peptides, polypeptides, denatured proteins and/or antigens are added to the denatured protein column to bind with the HSP complexes, thereby removing these complexes from the column and forming an HSP-peptide complex which is eluted.

A preferred denatured protein matrix for the present invention can be formed by adding gelatin-agarose beads to a standard chromatography column.

One method for obtaining purified heat shock proteins for the present invention is to use a gelatin-agarose method such as that described in Nandan et al., "A rapid single-step purification method for immunogenic members of the hsp family; validation and application," in *Journal of Immunological Methods* (1994), 176: 255–263. In this method of purification, cell lysates containing heat shock proteins are mixed with gelatin-agarose beads to bind the heat shock proteins to the beads. ATP is then added to the beads to release purified heat shock proteins.

Instead of synthesizing pure HSP-peptide complexes, it is often desirable to elute the HSP-peptide complex as an ADP-HSP-peptide complex. As described in co-pending patent application Ser. No. 08/717,239, such ADP-HSP-peptide complexes are stable and may be used to develop vaccines or immunotherapeutic tools for tumors and for infectious diseases. These ADP-HSP-peptide complexes can be formed in a number of ways. Preferably such complexes are formed by adding the heat shock protein to the denatured protein matrix in the form of an ADP-heat shock protein complex so that the HSP-peptide complexes synthesized in the column will include complexed ADP. To form the ADP-heat shock protein complex, the purified heat shock protein is mixed with ADP. A solution containing the ADP-heat shock protein complex is then added to an agarose-gelatin matrix to bind the heat shock protein to the denatured protein or gelatin. Because the denatured protein in the column binds to a different site on the heat shock protein than the ADP does, the ADP remains complexed to the heat shock protein, even when it is bound to the denatured protein in the column. A peptide complexing solution containing a peptide complexing agent is then added to the column to release the ADP-HSP complex as an ADP-HSP-peptide complex by binding to the peptide binding site on the HSP.

In addition to the process described above, there are a number of other ways of insuring that ADP is complexed to at least some of the eluted HSP-peptide complexes that are eluted. For example, ADP can be added to an HSP-containing solution, such as a cell lysate, before, after or at the same time as the HSP-containing solution is added to the denatured protein matrix. Also, where the HSP is added to the matrix as part of a solution or cell lysate containing ATP, ADP-HSP-peptide complexes can be synthesized by converting ATP to ADP in the cell lysate either before or after it is added to the matrix. One method for converting ATP to ADP in a cell lysate is to add glucose and hexokinase to the lysate containing ATP and let the lysate sit a room temperature for a period of time. Other suitable methods for converting ATP to ADP are described in Lehninger, *Biochemistry*, (New York: Worth Publishers, 1970), p. 299.

Some of the peptides suitable for use as peptide complexing agents in the present invention include those described in U.S. Pat. Nos. 5,348,864 (vav mouse oncogene); 5,320,941 (protein sequence of the mas oncogene and polypeptides derived therefrom); 5,614,192 (peptides capable of binding to T-cell receptors); and 5,550,214 (peptide capable of binding in the HLA-A2 binding cleft and capable of stimulating proliferation of cytotoxic T-lymphocytes); the entire disclosure and contents of which are hereby incorporated by reference. Other suitable peptides are listed in Table 1 of Figures 1A to 1E.

The peptide complexing agents are typically obtained from purified cell lysates. The cells from which the peptide complexing agents may be obtained from the same or different individual as the heat shock proteins to which they are complexed. The heat shock protein and peptide complexing agents may even be obtained from different species and either the heat shock protein or peptide complexing agent can be formed synthetically.

Although there are many heat shock proteins that may be used in the method of the present invention, heat shock proteins that have proven particularly useful include members of the hsp60 family, hsp70 family, hsp90 family and the hsp104–105 family.

Members of the hsp60 family include hsp60, hsp65, rubisco binding protein, and TCP-1 in eukaryotes; GroEl/GroES in prokaryotes; and Mif4 and TCP1 alpha and beta in yeast.

Members of the hsp70 family include DnaK proteins from prokaryotes, Ssa, Ssb, and Ssc from yeast, hsp70, Grp75 and Grp78(Bip) from eukaryotes. FIG. 1 is a drawing of a western blot of fractions taken from a purification using the method of the invention. The elution was started at fraction #10 and hsp70 protein appears in fraction #14.

Members of the hsp90 family include hsp90, gp96 and grp94.

Members of the hsp104–105 family include hsp105 and hspl110.

In another preferred embodiment, the present invention provides an apparatus for synthesizing heat shock protein-peptide complexes. Such an apparatus may be created by adding a desired heat shock protein or ADP-heat shock protein complex to a denatured protein matrix, as described above for the method of the present invention, to form a column having heat shock proteins bound therein. Such a column can be used to form a desired HSP-peptide complex or ADP-HSP-peptide complex by adding a peptide complexing agent to the column to elute the HSP-peptide complex or ADP-HSP-peptide complex, respectively, as described above for the method of the present invention.

The invention will now be described by way of example. The following example is illustrative and are not meant to limit the scope of the invention which is set forth by the appended claims.

EXAMPLE

Heat shock proteins from cells or sub-cellular fractions are solubilized in lysis buffer (20 mM Tris-HCl pH 7.5, 0.15 M NaCl, 1% Triton X-100) containing a cocktail of protease inhibitors. This cocktail consists of 25 $\mu$g/ml of leupeptin, 25 $\mu$g/ml of E64 antipain and 0.5 mM (polymethylsulfonyl fluoride). The lysate is centrifuged at 10,0000×g for 20 min. at 4° C. to remove insoluble materials. The supernatant is incubated with appropriate amounts of gelatin-agarose beads by mixing for 2 hours at 25° C. This incubation will result in a gelatin-HSP(ADP)-peptide complex. The beads are collected by centrifugation and washed three times with a buffer adjusted to 0.5 M NaCI, and once with 5mM Hepes, pH 7.5. Bound heat shock proteins are released by incubating the gelatin agarose beads with a solution containing a peptide or peptides representing the tumor or viral antigen. The heat shock protein-peptide complexes can then be used as a vaccine. Examples of suitable peptides that can be bound to heat shock proteins includes those found in Table 1 of Figures 1A to 1E.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A method for synthesizing heat shock protein complexes comprising the steps of:

adding a heat shock protein to a denatured protein matrix to bind the heat shock protein to the matrix; and adding a complexing solution comprising a peptide to elute a heat shock protein-peptide complex.

2. The method of claim 1, wherein said heat shock protein added to the matrix is complexed with ADP.

3. The method of claim 2, wherein said eluted heat shock protein-peptide complex comprises an ADP-heat shock protein peptide complex.

4. The method of claim 1, wherein said heat shock protein is added to the matrix as part of a solution containing said heat shock protein and said method further comprises the step of adding ADP to said heat shock protein-containing solution.

5. The method of claim 4, wherein ADP is added to said heat shock protein-containing solution prior to said heat shock protein-containing solution being added to the matrix.

6. The method of claim 4, wherein ADP is added to said heat shock protein-containing solution after said heat shock protein containing solution is added to the matrix.

7. The method of claim 4, wherein ADP is added to said heat shock protein-containing solution at the same time as said heat shock protein-containing solution is added to the matrix.

8. The method of claim 1, wherein said heat shock protein is added to the matrix as part of a heat shock protein-containing solution which includes ATP and the method further comprises the step of converting ATP in the heat shock protein-containing solution to ADP.

9. The method of claim 1, wherein said heat shock protein is added to the matrix as part of a cell lysate.

10. The method of claim 1 wherein the heat shock protein is selected from the group consisting of: hsp60, hsp65, rubisco binding protein and TCP-1 from eukaryotes; and GroEL/GroES, Mif4, TCPalpha and TCPbeta from yeast.

11. The method of claim 1 wherein the heat shock protein is selected from the group consisting of: hsp104, hsp105 and hsp110.

12. The method of claim 1 wherein the heat shock protein is selected from the group consisting of: DnaK proteins from prokaryotes; Ssa, Ssb, and Ssc from yeast; and hsp70, Grp75 and Grp78(Bip) from eukaryotes.

13. The method of claim 1 wherein the heat shock protein comprises one of the group consisting of: hsp90, gp96 and grp94.

14. The method of claim 1 wherein the peptide is from the same individual as the heat shock protein.

15. The method of claim 1 wherein the peptide and the heat shock protein are from different individuals.

16. The method of claim 1 wherein the peptide and the heat shock protein are from different species.

17. The method of claim 1 wherein the complexing solution comprises a cell lysate.

18. An apparatus for synthesizing heat shock protein-peptide complexes comprising a heat shock protein bound to a denatured protein matrix, said heat shock protein being complexed with ADP.

19. The apparatus of claim 18 wherein said denatured protein matrix comprises a denatured protein column.

20. The apparatus of claim 18 wherein the heat shock protein is selected from the group consisting of: hsp60, hsp65, rubisco binding protein and TCP-1 from eukaryotes; and GroEL/GroES, Mif4, TCPalpha and TCPbeta from yeast.

21. The apparatus of claim 18 wherein the heat shock protein is selected from the group consisting of: hsp104, hsp105 and hsp110.

22. The apparatus of claim 18 wherein the heat shock protein is selected from the group consisting of: DnaK proteins from prokaryotes; Ssa, Ssb, and Ssc from yeast; and hsp70, Grp75 and Grp78(Bip) from eukaryotes.

23. The apparatus of claim 18 wherein the heat shock protein is selected from the group consisting of: hsp90, gp96 and grp94.

* * * * *

SEQUENCE LISTING

```
<160> NUMBER OF SEQ ID NOS: 114

<210> SEQ ID NO 1
<211> LENGTH: 9
<212> TYPE: PRT
<213> ORGANISM: human

<400> SEQUENCE: 1

Glu Ala Asp Pro Thr Gly His Ser Tyr
  1               5


<210> SEQ ID NO 2
<211> LENGTH: 17
<212> TYPE: PRT
<213> ORGANISM: Feline immunodeficiency virus

<400> SEQUENCE: 2
```

-continued

Arg Ala Ile Ser Ser Trp Lys Gln Arg Asn Arg Trp Glu Trp Arg Pro
1 5 10 15

Asp

<210> SEQ ID NO 3
<211> LENGTH: 10
<212> TYPE: PRT
<213> ORGANISM: Feline immunodeficiency virus

<400> SEQUENCE: 3

Arg Ala Ile Ser Ser Trp Lys Gln Arg Asn
1 5 10

<210> SEQ ID NO 4
<211> LENGTH: 10
<212> TYPE: PRT
<213> ORGANISM: Feline immunodeficiency virus

<400> SEQUENCE: 4

Ser Trp Lys Gln Arg Asn Arg Trp Glu Trp
1 5 10

<210> SEQ ID NO 5
<211> LENGTH: 10
<212> TYPE: PRT
<213> ORGANISM: Feline immunodeficiency virus

<400> SEQUENCE: 5

Gln Arg Asn Arg Trp Glu Trp Arg Pro Asp
1 5 10

<210> SEQ ID NO 6
<211> LENGTH: 19
<212> TYPE: PRT
<213> ORGANISM: Foot-and-mouth disease virus

<400> SEQUENCE: 6

Ile Met Asp Arg Phe Val Lys Ile Asn Ser Leu Ser Pro Thr His Val
1 5 10 15

Ile Asp Leu

<210> SEQ ID NO 7
<211> LENGTH: 15
<212> TYPE: PRT
<213> ORGANISM: Foot-and-mouth disease virus

<400> SEQUENCE: 7

Pro Phe Gly His Leu Thr Lys Leu Glu Leu Pro Thr Asp His His
1 5 10 15

<210> SEQ ID NO 8
<211> LENGTH: 15
<212> TYPE: PRT
<213> ORGANISM: Foot-and-mouth disease virus

<400> SEQUENCE: 8

Ser Ile Ile Asn Asn Tyr Tyr Met Gln Gln Tyr Gln Asn Ser Met
1 5 10 15

<210> SEQ ID NO 9
<211> LENGTH: 35
<212> TYPE: PRT
<213> ORGANISM: human

<400> SEQUENCE: 9

Thr Tyr Ser Pro Ala Leu Lys Asn Met Phe Tyr Gln Leu Ala Lys Thr
1 5 10 15

Cys Pro Val Gln Leu Lys Met Phe Tyr Gln Leu Ala Lys Thr Cys Pro
20 25 30

Val Gln Leu
35

<210> SEQ ID NO 10
<211> LENGTH: 14
<212> TYPE: PRT
<213> ORGANISM: human

<400> SEQUENCE: 10

Lys Met Phe Tyr Gln Leu Ala Lys Thr Cys Pro Val Gln Leu
1 5 10

<210> SEQ ID NO 11
<211> LENGTH: 9
<212> TYPE: PRT
<213> ORGANISM: human

<400> SEQUENCE: 11

Phe Tyr Gln Leu Ala Thr Cys Pro Val
1 5

<210> SEQ ID NO 12
<211> LENGTH: 10
<212> TYPE: PRT
<213> ORGANISM: human

<400> SEQUENCE: 12

Phe Leu Gln Leu Ala Lys Thr Cys Pro Val
1 5 10

<210> SEQ ID NO 13
<211> LENGTH: 15
<212> TYPE: PRT
<213> ORGANISM: Human immunodeficiency virus

<400> SEQUENCE: 13

Arg Ile Gln Arg Gly Pro Gly Arg Ala Phe Val Thr Ile Gly Lys
1 5 10 15

<210> SEQ ID NO 14
<211> LENGTH: 15
<212> TYPE: PRT
<213> ORGANISM: Human immunodeficiency virus

<400> SEQUENCE: 14

Arg Ile His Ile Gly Pro Gly Arg Ala Phe Tyr Thr Thr Lys Asn
1 5 10 15

<210> SEQ ID NO 15
<211> LENGTH: 15
<212> TYPE: PRT
<213> ORGANISM: Human immunodeficiency virus

<400> SEQUENCE: 15

Ser Ile Thr Lys Gly Pro Gly Arg Val Ile Tyr Ala Thr Gly Gln
1 5 10 15

<210> SEQ ID NO 16
<211> LENGTH: 15

-continued

<212> TYPE: PRT
<213> ORGANISM: Human immunodeficiency virus

<400> SEQUENCE: 16

Thr Leu His Met Gly Pro Lys Arg Ala Phe Tyr Ala Thr Gly Asn
1 5 10 15

<210> SEQ ID NO 17
<211> LENGTH: 15
<212> TYPE: PRT
<213> ORGANISM: Human immunodeficiency virus

<400> SEQUENCE: 17

Ser Ile His Ile Gly Pro Gly Arg Ala Phe Tyr Thr Thr Gly Glu
1 5 10 15

<210> SEQ ID NO 18
<211> LENGTH: 15
<212> TYPE: PRT
<213> ORGANISM: Human immunodeficiency virus

<400> SEQUENCE: 18

Arg Ile His Ile Gly Pro Gly Arg Ala Phe Tyr Thr Thr Lys Asn
1 5 10 15

<210> SEQ ID NO 19
<211> LENGTH: 15
<212> TYPE: PRT
<213> ORGANISM: Human immunodeficiency virus

<400> SEQUENCE: 19

Ser Ile Arg Ile Gly Pro Gly Lys Val Phe Thr Ala Lys Gly Gly
1 5 10 15

<210> SEQ ID NO 20
<211> LENGTH: 15
<212> TYPE: PRT
<213> ORGANISM: Human immunodeficiency virus

<400> SEQUENCE: 20

Ser Ile Ser Ile Gly Pro Gly Arg Ala Phe Phe Ala Thr Thr Asp
1 5 10 15

<210> SEQ ID NO 21
<211> LENGTH: 15
<212> TYPE: PRT
<213> ORGANISM: Human immunodeficiency virus

<400> SEQUENCE: 21

Arg Ile His Ile Gly Pro Gly Arg Ala Phe Tyr Thr Thr Lys Asn
1 5 10 15

<210> SEQ ID NO 22
<211> LENGTH: 15
<212> TYPE: PRT
<213> ORGANISM: Human immunodeficiency virus

<400> SEQUENCE: 22

Ser Leu Ser Ile Gly Pro Gly Arg Ala Phe Arg Thr Arg Glu Ile
1 5 10 15

<210> SEQ ID NO 23
<211> LENGTH: 15
<212> TYPE: PRT

<213> ORGANISM: Human immunodeficiency virus

<400> SEQUENCE: 23

Gly Ile Ala Ile Gly Pro Gly Arg Thr Leu Tyr Ala Arg Glu Lys
1 5 10 15

<210> SEQ ID NO 24
<211> LENGTH: 15
<212> TYPE: PRT
<213> ORGANISM: Human immunodeficiency virus

<400> SEQUENCE: 24

Ser Ile Thr Lys Gly Pro Gly Arg Val Ile Tyr Ala Thr Gly Gln
1 5 10 15

<210> SEQ ID NO 25
<211> LENGTH: 15
<212> TYPE: PRT
<213> ORGANISM: Human immunodeficiency virus

<400> SEQUENCE: 25

Arg Val Thr Leu Gly Pro Gly Arg Val Trp Tyr Thr Thr Gly Glu
1 5 10 15

<210> SEQ ID NO 26
<211> LENGTH: 15
<212> TYPE: PRT
<213> ORGANISM: Human immunodeficiency virus

<400> SEQUENCE: 26

Ser Ile His Ile Gly Pro Gly Arg Ala Phe Tyr Ala Thr Gly Asp
1 5 10 15

<210> SEQ ID NO 27
<211> LENGTH: 15
<212> TYPE: PRT
<213> ORGANISM: Human immunodeficiency virus

<400> SEQUENCE: 27

Ser Ile Tyr Ile Gly Pro Gly Arg Ala Phe His Thr Thr Gly Arg
1 5 10 15

<210> SEQ ID NO 28
<211> LENGTH: 15
<212> TYPE: PRT
<213> ORGANISM: Human immunodeficiency virus

<400> SEQUENCE: 28

Arg Ile Gln Arg Gly Pro Gly Arg Ala Phe Val Thr Ile Gly Lys
1 5 10 15

<210> SEQ ID NO 29
<211> LENGTH: 15
<212> TYPE: PRT
<213> ORGANISM: Human immunodeficiency virus

<400> SEQUENCE: 29

Gly Ile His Phe Gly Pro Gly Gln Ala Leu Tyr Thr Thr Gly Ile
1 5 10 15

<210> SEQ ID NO 30
<211> LENGTH: 15
<212> TYPE: PRT
<213> ORGANISM: Human immunodeficiency virus

<400> SEQUENCE: 30

-continued

Ser Thr Pro Ile Gly Leu Gly Gln Ala Leu Tyr Thr Thr Arg Gly
1 5 10 15

<210> SEQ ID NO 31
<211> LENGTH: 15
<212> TYPE: PRT
<213> ORGANISM: Human immunodeficiency virus

<400> SEQUENCE: 31

Ser Thr Pro Ile Gly Leu Gly Gln Ala Leu Tyr Thr Thr Arg Ile
1 5 10 15

<210> SEQ ID NO 32
<211> LENGTH: 15
<212> TYPE: PRT
<213> ORGANISM: Human immunodeficiency virus

<400> SEQUENCE: 32

Arg Thr Pro Thr Gly Leu Gly Gln Ser Leu Tyr Thr Thr Arg Ser
1 5 10 15

<210> SEQ ID NO 33
<211> LENGTH: 16
<212> TYPE: PRT
<213> ORGANISM: Hepatitis C virus

<400> SEQUENCE: 33

Met Ser Tyr Ser Trp Thr Gly Ala Cys Val Thr Pro Cys Ala Ala Phe
1 5 10 15

<210> SEQ ID NO 34
<211> LENGTH: 16
<212> TYPE: PRT
<213> ORGANISM: Hepatitis C virus

<400> SEQUENCE: 34

Gly Phe Ala Asp Leu Met Gly Tyr Ile Pro Leu Val Gly Ala Pro Leu
1 5 10 15

<210> SEQ ID NO 35
<211> LENGTH: 10
<212> TYPE: PRT
<213> ORGANISM: Hepatitis C virus

<400> SEQUENCE: 35

Leu Met Gly Tyr Ile Pro Leu Val Gly Ala
1 5 10

<210> SEQ ID NO 36
<211> LENGTH: 17
<212> TYPE: PRT
<213> ORGANISM: human

<400> SEQUENCE: 36

Lys Leu Val Val Val Gly Ala Xaa Gly Val Gly Lys Ser Ala Leu Thr
1 5 10 15

Ile

<210> SEQ ID NO 37
<211> LENGTH: 12
<212> TYPE: PRT
<213> ORGANISM: Chlamydia trachomatis

<400> SEQUENCE: 37

Thr Ile Asn Lys Pro Lys Gly Tyr Thr Gly Lys Glu
1 5 10

<210> SEQ ID NO 38
<211> LENGTH: 9
<212> TYPE: PRT
<213> ORGANISM: Human immunodeficiency virus

<400> SEQUENCE: 38

His Ile Val Trp Ala Ser Arg Phe Leu
1 5

<210> SEQ ID NO 39
<211> LENGTH: 9
<212> TYPE: PRT
<213> ORGANISM: Human immunodeficiency virus

<400> SEQUENCE: 39

Ile Leu Gly Gln Leu Gln Pro Ser Leu
1 5

<210> SEQ ID NO 40
<211> LENGTH: 9
<212> TYPE: PRT
<213> ORGANISM: Human immunodeficiency virus

<400> SEQUENCE: 40

Ser Leu Gln Thr Gly Ser Glu Glu Leu
1 5

<210> SEQ ID NO 41
<211> LENGTH: 9
<212> TYPE: PRT
<213> ORGANISM: Human immunodeficiency virus

<400> SEQUENCE: 41

Glu Leu Arg Ser Leu Tyr Asn Thr Val
1 5

<210> SEQ ID NO 42
<211> LENGTH: 9
<212> TYPE: PRT
<213> ORGANISM: Human immunodeficiency virus

<400> SEQUENCE: 42

Ser Leu Tyr Asn Thr Val Ala Thr Leu
1 5

<210> SEQ ID NO 43
<211> LENGTH: 9
<212> TYPE: PRT
<213> ORGANISM: Human immunodeficiency virus

<400> SEQUENCE: 43

Glu Ile Lys Asp Thr Lys Glu Ala Leu
1 5

<210> SEQ ID NO 44
<211> LENGTH: 9
<212> TYPE: PRT
<213> ORGANISM: Human immunodeficiency virus

<400> SEQUENCE: 44

Thr Leu Asn Ala Trp Val Lys Val Val
1 5

<210> SEQ ID NO 45
<211> LENGTH: 9
<212> TYPE: PRT
<213> ORGANISM: Human immunodeficiency virus

<400> SEQUENCE: 45

Asp Leu Asn Thr Met Leu Asn Thr Val
1 5

<210> SEQ ID NO 46
<211> LENGTH: 9
<212> TYPE: PRT
<213> ORGANISM: Human immunodeficiency virus

<400> SEQUENCE: 46

Asp Ile Ala Gly Thr Thr Ser Thr Leu
1 5

<210> SEQ ID NO 47
<211> LENGTH: 9
<212> TYPE: PRT
<213> ORGANISM: Human immunodeficiency virus

<400> SEQUENCE: 47

Thr Leu Gln Glu Gln Ile Gly Trp Met
1 5

<210> SEQ ID NO 48
<211> LENGTH: 9
<212> TYPE: PRT
<213> ORGANISM: Human immunodeficiency virus

<400> SEQUENCE: 48

Glu Ile Tyr Lys Arg Trp Ile Leu Leu
1 5

<210> SEQ ID NO 49
<211> LENGTH: 9
<212> TYPE: PRT
<213> ORGANISM: Human immunodeficiency virus

<400> SEQUENCE: 49

Ile Ile Leu Gly Leu Asn Lys Ile Val
1 5

<210> SEQ ID NO 50
<211> LENGTH: 8
<212> TYPE: PRT
<213> ORGANISM: Human immunodeficiency virus

<400> SEQUENCE: 50

Phe Met Met Thr Ala Cys Gly Val
1 5

<210> SEQ ID NO 51
<211> LENGTH: 9
<212> TYPE: PRT
<213> ORGANISM: Human immunodeficiency virus

<400> SEQUENCE: 51

Val Leu Ala Glu Ala Met Ser Gln Val
1 5

<210> SEQ ID NO 52
<211> LENGTH: 9

-continued

<212> TYPE: PRT
<213> ORGANISM: Human immunodeficiency virus

<400> SEQUENCE: 52

Pro Ile Asp Lys Glu Leu Tyr Pro Leu
1 5

<210> SEQ ID NO 53
<211> LENGTH: 9
<212> TYPE: PRT
<213> ORGANISM: Human immunodeficiency virus

<400> SEQUENCE: 53

Leu Leu Thr Gln Ile Gly Cys Thr Leu
1 5

<210> SEQ ID NO 54
<211> LENGTH: 9
<212> TYPE: PRT
<213> ORGANISM: Human immunodeficiency virus

<400> SEQUENCE: 54

Pro Ile Glu Thr Val Pro Val Lys Leu
1 5

<210> SEQ ID NO 55
<211> LENGTH: 9
<212> TYPE: PRT
<213> ORGANISM: Human immunodeficiency virus

<400> SEQUENCE: 55

Ala Leu Val Glu Ile Cys Thr Glu Met
1 5

<210> SEQ ID NO 56
<211> LENGTH: 9
<212> TYPE: PRT
<213> ORGANISM: Human immunodeficiency virus

<400> SEQUENCE: 56

Gly Ile Arg Tyr Gln Tyr Asn Val Leu
1 5

<210> SEQ ID NO 57
<211> LENGTH: 9
<212> TYPE: PRT
<213> ORGANISM: Human immunodeficiency virus

<400> SEQUENCE: 57

Tyr Ile Tyr Gln Tyr Met Asp Asp Leu
1 5

<210> SEQ ID NO 58
<211> LENGTH: 9
<212> TYPE: PRT
<213> ORGANISM: Human immunodeficiency virus

<400> SEQUENCE: 58

Lys Ile Glu Glu Leu Arg Gln His Leu
1 5

<210> SEQ ID NO 59
<211> LENGTH: 9
<212> TYPE: PRT
<213> ORGANISM: Human immunodeficiency virus

<400> SEQUENCE: 59

-continued

Glu Leu His Pro Asp Lys Trp Thr Val
1 5

<210> SEQ ID NO 60
<211> LENGTH: 9
<212> TYPE: PRT
<213> ORGANISM: Human immunodeficiency virus

<400> SEQUENCE: 60

Asp Ile Gln Lys Leu Val Gly Lys Leu
1 5

<210> SEQ ID NO 61
<211> LENGTH: 9
<212> TYPE: PRT
<213> ORGANISM: Human immunodeficiency virus

<400> SEQUENCE: 61

Lys Leu Lys Arg Gly Thr Lys Ala Leu
1 5

<210> SEQ ID NO 62
<211> LENGTH: 9
<212> TYPE: PRT
<213> ORGANISM: Human immunodeficiency virus

<400> SEQUENCE: 62

Glu Leu Ala Glu Asn Arg Glu Ile Leu
1 5

<210> SEQ ID NO 63
<211> LENGTH: 9
<212> TYPE: PRT
<213> ORGANISM: Human immunodeficiency virus

<400> SEQUENCE: 63

Ile Leu Lys Glu Pro Val His Gly Val
1 5

<210> SEQ ID NO 64
<211> LENGTH: 8
<212> TYPE: PRT
<213> ORGANISM: Human immunodeficiency virus

<400> SEQUENCE: 64

Pro Leu Val Lys Leu Trp Tyr Leu
1 5

<210> SEQ ID NO 65
<211> LENGTH: 9
<212> TYPE: PRT
<213> ORGANISM: Human immunodeficiency virus

<400> SEQUENCE: 65

Glu Leu Gln Ala Ile Tyr Leu Ala Leu
1 5

<210> SEQ ID NO 66
<211> LENGTH: 9
<212> TYPE: PRT
<213> ORGANISM: Human immunodeficiency virus

<400> SEQUENCE: 66

Tyr Leu Ala Leu Gln Asp Ser Gly Leu
1 5

<210> SEQ ID NO 67
<211> LENGTH: 9
<212> TYPE: PRT
<213> ORGANISM: Human immunodeficiency virus

<400> SEQUENCE: 67

Ala Leu Gln Asp Ser Gly Leu Glu Val
1 5

<210> SEQ ID NO 68
<211> LENGTH: 9
<212> TYPE: PRT
<213> ORGANISM: Human immunodeficiency virus

<400> SEQUENCE: 68

Leu Ile Lys Lys Glu Lys Val Tyr Leu
1 5

<210> SEQ ID NO 69
<211> LENGTH: 9
<212> TYPE: PRT
<213> ORGANISM: Human immunodeficiency virus

<400> SEQUENCE: 69

His Leu Glu Gly Lys Val Ile Leu Val
1 5

<210> SEQ ID NO 70
<211> LENGTH: 9
<212> TYPE: PRT
<213> ORGANISM: Human immunodeficiency virus

<400> SEQUENCE: 70

Glu Leu Lys Lys Ile Ile Gly Gln Val
1 5

<210> SEQ ID NO 71
<211> LENGTH: 9
<212> TYPE: PRT
<213> ORGANISM: Human immunodeficiency virus

<400> SEQUENCE: 71

Pro Leu Trp Lys Gly Pro Ala Lys Leu
1 5

<210> SEQ ID NO 72
<211> LENGTH: 9
<212> TYPE: PRT
<213> ORGANISM: Human immunodeficiency virus

<400> SEQUENCE: 72

Leu Leu Trp Lys Gly Glu Gly Ala Val
1 5

<210> SEQ ID NO 73
<211> LENGTH: 9
<212> TYPE: PRT
<213> ORGANISM: Human immunodeficiency virus

<400> SEQUENCE: 73

Ile Ile Arg Asp Tyr Gly Lys Gln Met
1 5

<210> SEQ ID NO 74
<211> LENGTH: 9

-continued

<212> TYPE: PRT
<213> ORGANISM: Human immunodeficiency virus

<400> SEQUENCE: 74

Met Ile Val Trp Gln Val Asp Arg Met
1 5

<210> SEQ ID NO 75
<211> LENGTH: 9
<212> TYPE: PRT
<213> ORGANISM: Human immunodeficiency virus

<400> SEQUENCE: 75

Arg Ile Arg Thr Trp Lys Ser Leu Val
1 5

<210> SEQ ID NO 76
<211> LENGTH: 9
<212> TYPE: PRT
<213> ORGANISM: Human immunodeficiency virus

<400> SEQUENCE: 76

Asp Leu Ala Asp Gln Leu Ile His Leu
1 5

<210> SEQ ID NO 77
<211> LENGTH: 9
<212> TYPE: PRT
<213> ORGANISM: Human immunodeficiency virus

<400> SEQUENCE: 77

Lys Ile Lys Pro Pro Leu Pro Ser Val
1 5

<210> SEQ ID NO 78
<211> LENGTH: 9
<212> TYPE: PRT
<213> ORGANISM: Human immunodeficiency virus

<400> SEQUENCE: 78

Met Ile Cys Ser Ala Thr Glu Lys Leu
1 5

<210> SEQ ID NO 79
<211> LENGTH: 9
<212> TYPE: PRT
<213> ORGANISM: Human immunodeficiency virus

<400> SEQUENCE: 79

Ile Ile Leu Ser Trp Asp Gln Ser Leu
1 5

<210> SEQ ID NO 80
<211> LENGTH: 9
<212> TYPE: PRT
<213> ORGANISM: Human immunodeficiency virus

<400> SEQUENCE: 80

Lys Leu Thr Ser Leu Cys Val Ser Leu
1 5

<210> SEQ ID NO 81
<211> LENGTH: 9
<212> TYPE: PRT
<213> ORGANISM: Human immunodeficiency virus

<400> SEQUENCE: 81

Lys Leu Thr Ser Cys Asn Thr Ser Val
1 5

<210> SEQ ID NO 82
<211> LENGTH: 9
<212> TYPE: PRT
<213> ORGANISM: Human immunodeficiency virus

<400> SEQUENCE: 82

Val Ile Thr Gln Ala Cys Pro Lys Val
1 5

<210> SEQ ID NO 83
<211> LENGTH: 9
<212> TYPE: PRT
<213> ORGANISM: Human immunodeficiency virus

<400> SEQUENCE: 83

Ile Ile Val Gln Leu Asn Thr Ser Val
1 5

<210> SEQ ID NO 84
<211> LENGTH: 9
<212> TYPE: PRT
<213> ORGANISM: Human immunodeficiency virus

<400> SEQUENCE: 84

Thr Leu Lys Gln Ile Ala Ser Lys Leu
1 5

<210> SEQ ID NO 85
<211> LENGTH: 9
<212> TYPE: PRT
<213> ORGANISM: Human immunodeficiency virus

<400> SEQUENCE: 85

Ala Ile Ile Asn Met Trp Gln Lys Val
1 5

<210> SEQ ID NO 86
<211> LENGTH: 9
<212> TYPE: PRT
<213> ORGANISM: Human immunodeficiency virus

<400> SEQUENCE: 86

Phe Leu Gly Ala Ala Gly Ser Thr Met
1 5

<210> SEQ ID NO 87
<211> LENGTH: 9
<212> TYPE: PRT
<213> ORGANISM: Human immunodeficiency virus

<400> SEQUENCE: 87

Thr Leu Thr Val Gln Ala Arg Gln Leu
1 5

<210> SEQ ID NO 88
<211> LENGTH: 9
<212> TYPE: PRT
<213> ORGANISM: Human immunodeficiency virus

<400> SEQUENCE: 88

Gly Ile Val Gln Gln Gln Asn Asn Leu
1 5

<210> SEQ ID NO 89
<211> LENGTH: 9
<212> TYPE: PRT
<213> ORGANISM: Human immunodeficiency virus

<400> SEQUENCE: 89

Ala Ile Glu Ala Gln Gln His Leu Leu
1 5

<210> SEQ ID NO 90
<211> LENGTH: 9
<212> TYPE: PRT
<213> ORGANISM: Human immunodeficiency virus

<400> SEQUENCE: 90

Gln Leu Gln Ala Arg Ile Leu Ala Val
1 5

<210> SEQ ID NO 91
<211> LENGTH: 9
<212> TYPE: PRT
<213> ORGANISM: Human immunodeficiency virus

<400> SEQUENCE: 91

Arg Ile Leu Ala Val Glu Arg Tyr Leu
1 5

<210> SEQ ID NO 92
<211> LENGTH: 9
<212> TYPE: PRT
<213> ORGANISM: Human immunodeficiency virus

<400> SEQUENCE: 92

Gly Ile Trp Gly Cys Ser Gly Lys Leu
1 5

<210> SEQ ID NO 93
<211> LENGTH: 9
<212> TYPE: PRT
<213> ORGANISM: Human immunodeficiency virus

<400> SEQUENCE: 93

Gln Ile Trp Asn His Thr Thr Trp Met
1 5

<210> SEQ ID NO 94
<211> LENGTH: 9
<212> TYPE: PRT
<213> ORGANISM: Human immunodeficiency virus

<400> SEQUENCE: 94

Tyr Ile Lys Leu Phe Ile Met Ile Val
1 5

<210> SEQ ID NO 95
<211> LENGTH: 9
<212> TYPE: PRT
<213> ORGANISM: Human immunodeficiency virus

<400> SEQUENCE: 95

Phe Ile Met Ile Val Gly Gly Leu Val
1 5

-continued

<210> SEQ ID NO 96
<211> LENGTH: 9
<212> TYPE: PRT
<213> ORGANISM: Human immunodeficiency virus

<400> SEQUENCE: 96

Met Ile Val Gly Gly Leu Val Gly Leu
1 5

<210> SEQ ID NO 97
<211> LENGTH: 9
<212> TYPE: PRT
<213> ORGANISM: Human immunodeficiency virus

<400> SEQUENCE: 97

Gly Leu Arg Ile Val Phe Ala Val Leu
1 5

<210> SEQ ID NO 98
<211> LENGTH: 9
<212> TYPE: PRT
<213> ORGANISM: Human immunodeficiency virus

<400> SEQUENCE: 98

Ser Ile Arg Leu Val Asn Gly Ser Leu
1 5

<210> SEQ ID NO 99
<211> LENGTH: 9
<212> TYPE: PRT
<213> ORGANISM: Human immunodeficiency virus

<400> SEQUENCE: 99

Arg Leu Val Asn Gly Ser Leu Ala Leu
1 5

<210> SEQ ID NO 100
<211> LENGTH: 9
<212> TYPE: PRT
<213> ORGANISM: Human immunodeficiency virus

<400> SEQUENCE: 100

Ser Leu Ala Leu Ile Trp Asp Asp Leu
1 5

<210> SEQ ID NO 101
<211> LENGTH: 9
<212> TYPE: PRT
<213> ORGANISM: Human immunodeficiency virus

<400> SEQUENCE: 101

Leu Ile Trp Asp Asp Leu Arg Ser Leu
1 5

<210> SEQ ID NO 102
<211> LENGTH: 9
<212> TYPE: PRT
<213> ORGANISM: Human immunodeficiency virus

<400> SEQUENCE: 102

Arg Leu Arg Asp Leu Leu Leu Ile Val
1 5

<210> SEQ ID NO 103
<211> LENGTH: 9
<212> TYPE: PRT

<213> ORGANISM: Human immunodeficiency virus

<400> SEQUENCE: 103

Leu Leu Leu Ile Val Thr Arg Ile Val
1 5

<210> SEQ ID NO 104
<211> LENGTH: 9
<212> TYPE: PRT
<213> ORGANISM: Human immunodeficiency virus

<400> SEQUENCE: 104

Leu Ile Val Thr Arg Ile Val Glu Leu
1 5

<210> SEQ ID NO 105
<211> LENGTH: 9
<212> TYPE: PRT
<213> ORGANISM: Human immunodeficiency virus

<400> SEQUENCE: 105

Leu Leu Gln Tyr Trp Ser Gln Glu Leu
1 5

<210> SEQ ID NO 106
<211> LENGTH: 9
<212> TYPE: PRT
<213> ORGANISM: Human immunodeficiency virus

<400> SEQUENCE: 106

Glu Leu Lys Asn Ser Ala Val Ser Leu
1 5

<210> SEQ ID NO 107
<211> LENGTH: 9
<212> TYPE: PRT
<213> ORGANISM: Human immunodeficiency virus

<400> SEQUENCE: 107

Leu Leu Asn Ala Thr Ala Ile Ala Val
1 5

<210> SEQ ID NO 108
<211> LENGTH: 9
<212> TYPE: PRT
<213> ORGANISM: Human immunodeficiency virus

<400> SEQUENCE: 108

Ala Ile Ile Arg Ile Leu Gln Gln Leu
1 5

<210> SEQ ID NO 109
<211> LENGTH: 9
<212> TYPE: PRT
<213> ORGANISM: Human immunodeficiency virus

<400> SEQUENCE: 109

Ile Ile Arg Ile Leu Gln Gln Leu Leu
1 5

<210> SEQ ID NO 110
<211> LENGTH: 9
<212> TYPE: PRT
<213> ORGANISM: Human immunodeficiency virus

<400> SEQUENCE: 110

-continued

```
Tyr Leu Gly Arg Ser Ala Glu Pro Val
  1               5


<210> SEQ ID NO 111
<211> LENGTH: 9
<212> TYPE: PRT
<213> ORGANISM: Human immunodeficiency virus

<400> SEQUENCE: 111

Gln Ile Leu Val Glu Ser Pro Thr Val
  1               5


<210> SEQ ID NO 112
<211> LENGTH: 9
<212> TYPE: PRT
<213> ORGANISM: Human immunodeficiency virus

<400> SEQUENCE: 112

Ile Leu Val Glu Ser Pro Thr Val Leu
  1               5


<210> SEQ ID NO 113
<211> LENGTH: 9
<212> TYPE: PRT
<213> ORGANISM: Human immunodeficiency virus

<400> SEQUENCE: 113

Gln Ile Ala Ile Val Ala Ala Leu Val
  1               5


<210> SEQ ID NO 114
<211> LENGTH: 9
<212> TYPE: PRT
<213> ORGANISM: Human immunodeficiency virus

<400> SEQUENCE: 114

Gly Met Asp Asp Pro Glu Lys Glu Val
  1               5
```